(12) United States Patent
Shang

(10) Patent No.: US 10,736,614 B2
(45) Date of Patent: Aug. 11, 2020

(54) INTRAVASCULAR MEMORY METAL PUNCTURE NEEDLE AND USE THEREOF

(71) Applicant: Hua Shang, Jiangsu (CN)

(72) Inventor: Hua Shang, Jiangsu (CN)

( * ) Notice: Subject to any disclaimer, the term of this patent is extended or adjusted under 35 U.S.C. 154(b) by 0 days.

(21) Appl. No.: 16/373,843

(22) Filed: Apr. 3, 2019

(65) Prior Publication Data

US 2020/0029942 A1 Jan. 30, 2020

Related U.S. Application Data

(63) Continuation of application No. PCT/CN2018/097463, filed on Jul. 27, 2018.

(51) Int. Cl.
| | |
|---|---|
| *A61B 10/02* | (2006.01) |
| *A61B 5/00* | (2006.01) |
| *A61B 10/04* | (2006.01) |
| *A61B 17/34* | (2006.01) |

(52) U.S. Cl.
CPC ........ *A61B 10/0266* (2013.01); *A61B 5/6848* (2013.01); *A61B 10/04* (2013.01); *A61B 17/34* (2013.01); *A61B 2010/045* (2013.01)

(58) Field of Classification Search
CPC ............ A61B 10/0266; A61B 5/15119; A61B 2010/045
See application file for complete search history.

(56) References Cited

U.S. PATENT DOCUMENTS

| 9,925,389 B1* | 3/2018 | Shang ................... A61N 5/062 |
| 2010/0234866 A1* | 9/2010 | Arcenio ............. A61B 17/1671 |
| | | 606/170 |
| 2014/0142602 A1* | 5/2014 | Polo ....................... A61B 10/02 |
| | | 606/174 |

\* cited by examiner

*Primary Examiner* — Daniel L Cerioni
*Assistant Examiner* — Yasmeen S Warsi
(74) *Attorney, Agent, or Firm* — Hauptman Ham, LLP

(57) ABSTRACT

This disclosure provides an intravascular memory metal puncture needle and the use thereof. The puncture needle comprises a split-shaped structure capable of opening and closing, as well as a metal spiral hollow tube including a plurality of spiral coils, wherein the split-shaped structure and the metal spiral tube are made of memory metal, and the split-shaped structure is composed of a plurality of tapered petals; when the temperature is T1, the pitch between two adjacent spiral coils in the metal spiral tube is decreased, each of tapered petals in the split-shaped structure is closed; when the temperature is T0, the pitch between two adjacent spiral coils in the metal spiral tube is increased, and each of tapered petals is opened. The puncture needle achieves synergistic effect by matching the metal spiral tube with the split-shaped structure, so that it not only move well in the blood vessels, but also accurately pierce the blood vessel wall, and achieve effective sampling for biopsy.

9 Claims, 4 Drawing Sheets

INTRAVASCULAR MEMORY METAL PUNCTURE NEEDLE AND USE THEREOF

PRIORITY CLAIM

The present application is a continuing application of PCT Patent Application No. PCT/CN2018/097463, filed Jul. 27, 2018, which is incorporated herein by reference in its entirety.

TECHNICAL FIELD

The present disclosure relates to the technical field of medical instruments, in particular to an intravascular memory metal puncture needle and the use thereof.

BACKGROUND

With the continuous improvement of examination means and methods, the diagnostic accuracy of tumors is gradually improved. However, there are a large proportion of tumors that do not have typical imaging features and thus are difficult to be diagnosed. Accurate diagnosis requires the combination of clinic, imaging and pathology. Among them, the pathological diagnosis is crucial for selecting a suitable treatment program. Needling biopsy (also known as puncture biopsy) is the main way to obtain the pathological diagnosis. Needling biopsy is a method for taking out and analyzing tumor cells from a subject. The advantage of this method is simple. In particular, it can be performed under local anesthesia in the outpatient department, and the success rate thereof can be greatly improved under the guidance of CT, MRI ultrasound and fluoroscopy. However, needling biopsy is performed by directly puncturing to the tumor site via the body's surface through a puncture needle which is hard and unbendable. When the tumor is situated in a deeper site or a position rich in blood vessels of the body, the puncture needle will easily cause damage or bleeding to normal tissues of the patient, while the patient is also suffering from pain and fear.

At present, Seldinger arterial intubation technique is very mature. Under the guidance of clinical imaging medicine (X-ray, CT, MR, B-us, etc.), a delicate instrument, such as a special catheter or guidewire is inserted into the lesion via percutaneous vascular route or an original channel in human body, so as to achieve a diagnostic imaging and treatment. This technique uses the metal guidewire via percutaneous vascular route to enter the blood vessel and reach the lesion. This method is simple in operation, slight in damage, and does not need to suture the blood vessels. Thus, it completely replaces previous methods which need to cut open the blood vessels surgically, and becomes a basic operation technique of modern interventional radiology. This method has achieved good effects in tumor thrombosis and drug perfusion, intra-arterial irradiation, prevention of radiation damage, chemotherapy, preoperative embolization of tumor blood vessels, vasoactive drugs and alcohol perfusion, etc.

The present disclosure uses a memory metal to constitute an intravascular puncture needle, and the puncture needle reaches the tumor site under the guidance of the interventional guidewire through the Seldinger intubation technique, and realizes the puncture of the tumor by deforming the memory metal into a needle shape, so as to draw out tumor cells through a guide tube in the puncture needle. Compared with the traditional puncture needle, the device of this disclosure has the following characteristics: small damage to the normal tissue of the patient, low bleeding probability, and basically no pain and so on.

The method of sampling by entering a tumor tissue via passing through blood vessels seems to be simple, but it is quite difficult actually. This is because the tumor is buried inside the body in a certain depth. If you want to reach the tumor by passing through the blood vessels, it needs to pass through blood vessels up to 1 to 2 m long. In addition, both the diameters and the wall thicknesses of the blood vessels are different, and the conditions inside the blood vessels are complicated. Therefore, there are strict requirements for the catheter and the head portion of puncture needle, so that a little carelessness could lead to the inability to pass through such long blood vessels.

During the biopsy sampling, the operator holds the extracorporeal end of the device, and completes the sampling by passing through 1 m to 2 m long blood vessels and puncturing the tumor with the puncture needle, so the puncture needle is an extremely critical component. In addition, it is very difficult to accurately and conveniently operate the puncture needle to pass through the blood vessels, pierce the blood vessel walls, and enter the tumor tissue for sampling at far away from the needle, and thus requirements for the puncture needle are extremely strict. Moreover, there are many contradictions between the passing through blood vessels and puncturing, for example, passing through blood vessels needs to avoid damage to the inner wall of blood vessels, while puncturing needs to be able to accurately pierce the tumor tissue.

The puncture needle of this disclosure not only can avoid the damage to blood vessels during passing through blood vessels, but also can accurately puncture the tumor blood vessel walls and enter the tumor blood vessel wall tissues for sampling.

SUMMARY

In view of the above, an object of the present disclosure is to provide an intravascular memory metal puncture needle and the use thereof, so as to solve defects in the prior art.

The object of the present disclosure can be achieved by the following technical solutions.

An intravascular memory metal puncture needle is provided. In which the puncture needle comprises a split-shaped structure capable of opening and closing, as well as a metal spiral hollow tube including a plurality of spiral coils, wherein the split-shaped structure and the metal spiral tube are made of memory metal, and the split-shaped structure is composed of a plurality of tapered petals;

when the temperature is T1, the pitch between two adjacent spiral coils in the metal spiral tube is decreased, each of tapered petals in the split-shaped structure is closed, and thus the split-shaped structure exhibits a conical structure, to increase its strength to pierce the blood vessel walls;

when the temperature is T0, the pitch between two adjacent spiral coils in the metal spiral tube is increased to enhance flexibility of the device, so that it is able to move flexibly over long blood vessels in the body, and each of tapered petals is opened to allow a interventional guidewire to pass through during using, the split-shaped structure after opening is a cylindrical structure having a plurality of tapered notches on the wall, and the center of the cylindrical structure is an open cavity structure.

Further, an end with a larger diameter of the split-shaped structure is integrally connected to the metal spiral tube, the tapered petals have the same curvature at each point and are formed by arc-shaped surfaces.

Further, all of the tapered petals are identical in terms of shape and size.

Further, when the temperature is T1, two adjacent spiral coils in the metal spiral tube are closely abutted to form a more sealed structure, each of the tapered petals is closed, and two adjacent sides in two adjacent tapered petals are closely abutted, and then the split-shaped structure constitutes a fully enclosed conical structure.

Further, when the temperature is T0 and each of the tapered petals is opened, the diameters of the tapered petals are substantially consistent throughout, and are substantially consistent with that of the metal spiral tube.

Further, the tapered petal comprises a tail end and a tip end, and the width thereof is gradually decreased from the tail end to the tip end; when each of the tapered petals is closed, the diameter of the tail end is larger than that of the tip end; the temperature T0 is 37° C., the temperature T1 is 5° C.

Further, the width b of the memory alloy sheet for making the spiral coil is 0.3 to 1 mm; when the spiral coil is loosened (i.e., at temperature T0), the gap c between two adjacent spiral coils is 0.05 to 0.2 mm; when the pitch in the metal spiral tube is decreased (i.e., at temperature T1), the gap c between two adjacent spiral coils is less than 0.001 mm or even no gap therebetween.

Further, the length of the metal spiral tube is 4 to 10 mm, the length of the split-shaped structure is 3 to 10 mm; when the split-shaped structure is in the opened state, the outer diameter thereof is 0.4 mm and the inner diameter is 0.3 mm.

Further, in the tapered petals, the sides for abutting or separating from the adjacent tapered petals are inclined faces, and all the inclined faces of the tapered petals are consistent in direction.

Further, in the tapered petals, a first flexible layer may be provided on the sides or inclined faces for abutting or separating from the adjacent tapered petals, to make the abutment strength between the tapered petals more tight and the sealing therebetween better.

Further, a second flexible layer may be provided inside of the tip end of the tapered petal, to make when the split-shaped structure is closed, the abutment strength between the tapered petals more tight and the sealing therebetween better, and when a interventional guidewire is passed through the interior of the split-shaped structure, the bonding force with the interventional guidewire more stronger, the integration effect better, and the operation effect more practical.

The disclosure also relates to the use of the intravascular memory metal puncture needle, in which the puncture needle is used in the puncture of blood vessels or tissues or organs in the human body, and in the biopsy sampling of tumor in vivo; the method for using the puncture needle comprises:

(i) welding the metal spiral tube of the puncture needle with a long tube;

(ii) when the temperature T0 is 37° C., increasing the pitch in the metal spiral tube, opening the split-shaped structure, and then inserting a interventional guidewire from a free end of the long tube, through the metal spiral tube, and finally passing through the opened split-shaped structure, to move the structure in the blood vessels of the body;

(iii) after reaching the site to be punctured, withdrawing the interventional guidewire, inserting a syringe from the long tube, and respectively injecting physiological saline at T1 temperature into the metal spiral tube and the split-shaped structure when the injection needle reaches the puncture needle, and T1 is 5° C.; when the temperature of the puncture needle is gradually decreased to 5° C. with the injection of physiological saline, gradually decreasing the pitch of the metal spiral tube, and closing the split-shaped structure, so as to perform the puncture and sampling applications.

The present disclosure provides an intravascular memory metal puncture needle and the use thereof. The puncture needle mainly has the following effects:

First, one of the important functions of the memory alloy puncture needle is that: when passing through the blood vessels, the split-shaped structure keeps in the opened state, and an interventional guidewire is inserted in the split-shaped structure, each of tapered petals is attached to the outer wall of interventional guidewire. During the movement, there is almost no damage to the inner wall of the blood vessels; when reached the site to be punctured, it can change to the closed state to form a needle or conical shape by changing the temperature of the puncture needle, and thus the strength and hardness are greatly increased. The plurality of tapered petals can cooperate with each other, so as to easily puncture the walls of the blood vessels, e.g., the tumor blood vessels, enter the tumor tissue for the biopsy sampling. Such structural feature well solves the contradiction that it is required to avoid damage to the inner wall of the blood vessels when passing through the blood vessels and it is required to sharply puncture the inner wall of the blood vessels during biopsy sampling. Therefore, the structure of the puncture needle made of memory alloys makes it has good passage in the blood vessels and good puncture property to the tissue.

Second, another important effect brought out by using the memory alloy puncture needle is that: if the biopsy sampling is performed, it will stop injecting the physiological saline at T1 temperature after puncturing into the tissue such as a tumor, and the puncture needle is gradually restored to the opened state. When operating the hand-hold end to rotate the puncture needle or move it within a small area, as the plurality of tapered petals have a tapered structure, these tapered petals in the opened state would produce agitation and destruction effect in the small area of the tumor tissue, obtaining more and more effective tumor tissue during sampling, and thus resulting in better and more accurate biopsy results. Therefore, through skillfully using the memory alloy, the puncture needle can be changed between opening and closing, thereby achieving the passage of long blood vessels in the body, the piercing of tumor blood vessels and the entry of tumor tissue, assisting in effective biopsy sampling, and the like.

When the spiral coil of the metal spiral tube of this disclosure is loosened, the flexibility thereof is greatly increased in the case of having a certain strength, and thus it is convenient to move flexibly in long-distance and curved blood vessels; when the spiral coils are closed abutted together, the flexibility thereof is reduced, and the strength is greatly increased, and thus it can cooperate with the split-shaped structure to achieve the puncture of the blood vessel walls, and enter the tumor tissue for biopsy sampling.

Therefore, the present disclosure achieves a synergistic effect by cooperating the metal spiral tube and the split-shaped structure, so that the above objects or effects can be realized better. In addition, other additional technical features are further optimized for the technical solutions of the disclosure. These technical features are interactive and synergetic, jointly achieve the effects of smooth moving in the blood vessel, less damage to the blood vessel wall, piercing the wall of tumor blood vessel easier and successful entering the tumor tissue, and can perform the good and effectively sampling, finally achieve a more accurate biopsy effect.

Figure 1:
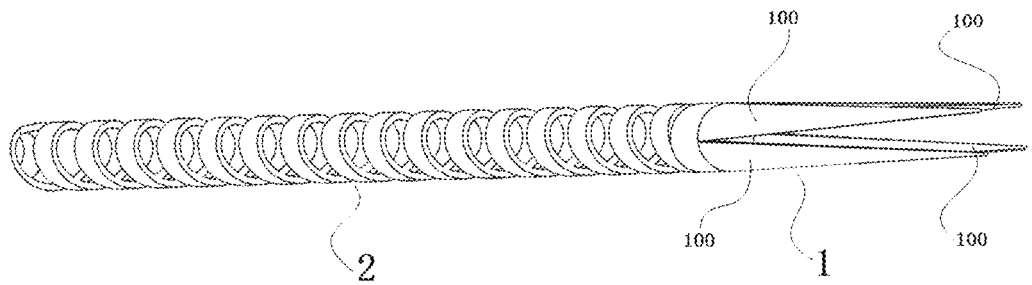
FIG. 1 is a schematic diagram illustrating the structure of the puncture needle according to Example 1 of the present disclosure.

LIST OF REFERENCE SYMBOLS 1 split-shaped structure
2 metal spiral tube
9 interventional guidewire
100 tapered petal
101 tail end
102 tip end
103 long tube
104 annular ring
105 inclined face

DETAILED DESCRIPTION

Various examples of the present disclosure are described below for details. Apparently, the described examples are only a part of examples in the present disclosure, rather than all of them. While the following contains many specific implementation details, they should not be construed as limitations on the scope of any claims, but rather as descriptions to particular examples. Based on the examples provided by the disclosure, other examples obtained by those skilled in the art without creative efforts are encompassed in the scope of the disclosure.

Example 1

Figure 4:
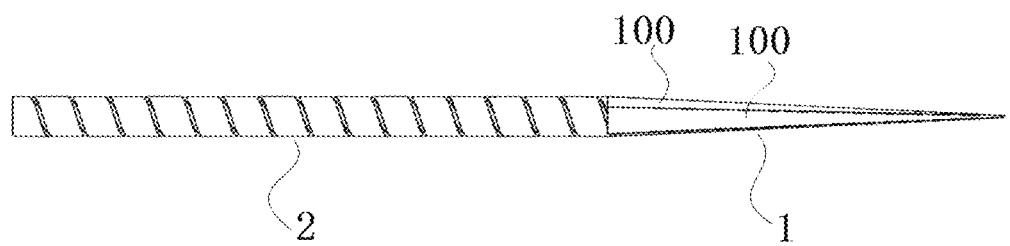
FIG. 4 is a schematic diagram illustrating the structure that the puncture needle according to Example 1 of the present disclosure includes a metal spiral tube at T1 temperature.
Figure 5:
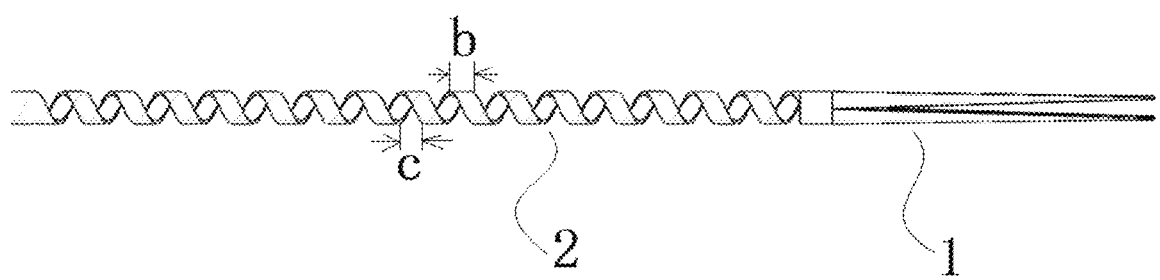
FIG. 5 is a schematic diagram illustrating the structure that the puncture needle according to Example 1 of the present disclosure is opened.

As shown in FIGS. 1, 4-5, an intravascular memory metal puncture needle is provided. This puncture needle comprises a split-shaped structure 1 capable of opening and closing, and a metal spiral tube 2 having a cavity inside. The split-shaped structure 1 and the metal spiral tube 2 are both made of memory metal including but not limited to nickel-titanium alloy, copper-nickel alloy, copper-aluminum alloy, copper-zinc alloy, etc.

Figure 2:
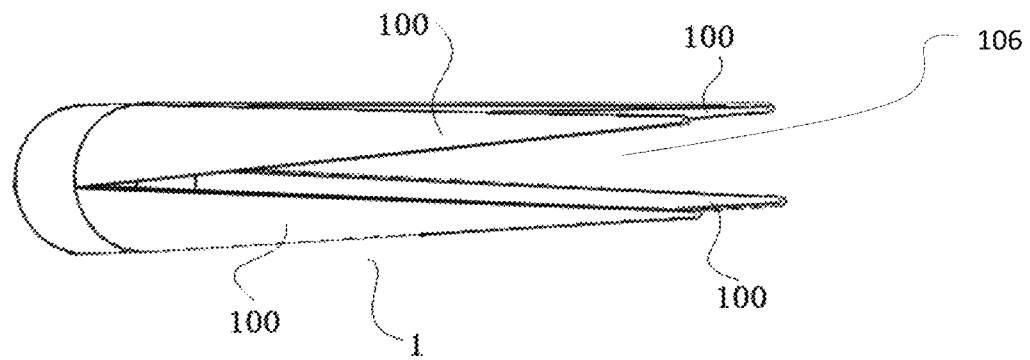
FIG. 2 is a schematic diagram illustrating the structure that the split-shaped structure according to Example 1 of the present disclosure is opened.
Figure 3:
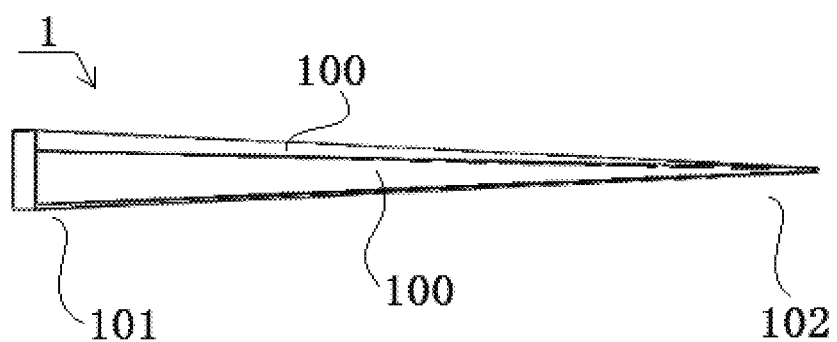
FIG. 3 is a schematic diagram illustrating the structure that the split-shaped structure according to Example 1 of the present disclosure is closed.

As shown in FIGS. 2-3, the split-shaped structure 1 is composed of a plurality of tapered petals 100. The plurality of tapered petals 100 may be identical multi-tapered petals, or may be different. However, whether they are identical or not, the split-shaped structure 1 has the following structural features: when each of tapered petals is closed, the split-shaped structure is a conical structure, as shown in FIG. 3, i.e., a needle-shaped structure having a large diameter at one end and a small diameter at the other end; when each of tapered petals is opened, the split-shaped structure is a cylindrical structure having a plurality of tapered notches on the wall, and the center of the cylindrical structure is an open cavity structure for passing through an interventional guidewire, as shown in FIG. 2.

As shown in FIG. 3, the tapered petal 100 comprises a tail end 101 and a tip end 102, and the width thereof is gradually decreased from the tail end 101 to the tip end 102. When each of tapered petals is closed, the diameter of the tail end 101 is larger than that of the tip end.

The metal spiral tube 2 is connected to the end having a larger diameter (i.e., the tail end 101) of the split-shaped structure 1. Preferably, the metal spiral tube and this end are integrally connected or integrally formed to possess a higher firmness or strength, and thus have a better effect when using.

Since the split-shaped structure is made by shape memory metal, it can deform to the closed or opened state according to the change in the temperature. For example, when the temperature is T0, the split-shaped structure is in the opened state, and when the temperature is T1, the split-shaped structure gets close together to form a needle shape, i.e., the conical structure. The temperature T0 may be set at 37° C., and the T1 may be set at 5° C.

Similarly, the metal spiral tube 2 is made of a memory alloy. When the temperature is T0, the pitch of two adjacent spiral coils in the metal spiral tube 2 is increased, and the diameter is also increased correspondingly. The outer diameter of the metal spiral tube 2 is about 0.35 to 0.45 mm, such as 0.4 mm Such structure makes it have certain rigidity while having an increased flexibility, so that it is suitable for passing through long-distance blood vessels. Meanwhile, at T0 temperature, the split-shaped structure 1 is in the opened state, as shown in FIG. 1; when the temperature is T1, the pitch in the metal spiral tube is decreased, and the diameter is also decreased correspondingly, the outer diameter is about 0.3 to 0.4 mm, such as 0.35 mm, 0.38 mm and the like. And, at the T1 temperature, the split-shaped structure 1 is in the closed state, which is convenient for puncturing the blood vessel wall. As shown in FIG. 4, the adjacent two spiral coils are brought together, and thus the flexibility would be decreased and the strength would be increased.

As a further preferred embodiment, the metal spiral tube 2 may have a spiral structure having spiral kerfs formed by laser cutting on a memory metal tube, so that it has a certain strength while increasing a certain flexibility. In addition, this spiral tube 2 has no elasticity and thus is essentially different from the spring. Any spring cannot achieve the function of the metal spiral tube 2 in this example.

As a further preferred embodiment, the length of the metal spiral tube 2 is 4 to 10 mm, such as 5 mm, 6 mm, 7 mm, 8 mm, etc. When the spiral coils are loosened, the out diameter is 0.4 mm, and the inner diameter is 0.3 mm.

The thickness of the metal spiral tube is 0.1 to 0.2 mm, such as 0.1 mm, 0.15 mm or 0.2 mm. The thickness is also important for the coordination of strength and flexibility. Too thick or too thin may affect the movement or strength of the puncture needle. When the pitch in the metal spiral tube 2 is increased, the length will be slightly longer; when the pitch is decreased, the length will be slightly smaller, but both should be within the above length range.

The length of the split-shaped structure is 3 to 10 mm, such as 5 mm. When the split-shaped structure is opened, the outer diameter thereof is 0.4 mm and the inner diameter is 0.3 mm.

As a further preferred embodiment, in the metal spiral tube 2, the width b of the memory alloy sheet for making the spiral coil is 0.3 to 1 mm. If the width b is too wider, the flexibility will be affected, and thus the flexibility of movement in the long-distance curved blood vessels will be affected. If the width b is too narrow, the strength will be insufficient, and thus it is impossible to pass through the long-distance blood vessels and reach the tumor tissue. When the spiral coil is loosened (i.e., at temperature T0), the gap c between two adjacent spiral coils is 0.05 to 0.2 mm. If the gap c is too wider, the strength will be insufficient, and if too narrow, the flexibility will be insufficient, as shown in FIG. 5. Therefore, the specifications of b and c are very important. Only under the effective coordination of the reasonable width b and the gap c, the puncture needle can pass through the long blood vessels in the body more stably and quickly, and reach the tumor blood vessels accurately. When the pitch in the metal spiral tube is decreased (i.e., at temperature T1), the gap c between two adjacent spiral coils is less than 0.001 mm or even no gap therebetween.

Preferably, when the temperature is T1, the pitch in the metal spiral tube 2 is decreased, the two adjacent spiral coils are closely abutted together, and the strength is greatly increased.

As a further preferred embodiment, the tapered petals are arc-shaped surfaces having same curvature at each point, so that a needle shaped structure having an conical shape is formed exactly after closing all of the tapered petals; and so that the split-shaped structure 1 can be stressed consistently everywhere and can be easier to move in the blood vessels, thereby making the damage more slight.

As a further preferred embodiment, all of the tapered petals 100 are identical in terms of shape and size. That is, preferably each of the tapered petals 100 is identical. When all the tapered petals 100 are identical, each of tapered petals exerts consistent force or is stressed consistently; when the split-shaped structure is closed, it shows as the needle-like structure having the stronger strength, which can puncture the tumor tissue more precisely. Thus, the biopsy sampling is more convenient and has better effects.

As a further preferred embodiment, when each of the tapered petals 100 is closed, two adjacent sides in the two adjacent tapered petals 100 are closely abutted, i.e., there is substantially no gap between the two adjacent tapered petals. The split-shaped structure constitutes a fully enclosed conical structure. Closely abutment with each other makes the formed conical structure having the stronger strength, a better puncture effect on the tissue, and more practical. In addition, the tight closure makes the formed conical structure having a good sealing effect. Therefore, after injecting low temperature physiological saline to close this structure, it just needs to continuously inject a small amount of physiological saline to maintain the closed state, providing sufficient time to puncture the tumor blood vessels and enter the interior of the tumor tissue.

As a further preferred embodiment, the split-shaped structure comprises 2 to 5 tapered petals, preferably 3 tapered petals or 4 tapered petals. If the number of petals is too few, the wrapping force on the tubular interventional guidewire will be unstable in all directions, and thus the movement of the structure in the blood vessels is poor. If the number of petals is too many, each tapered petal will be too small and cannot reach the desired strength.

Figure 6:
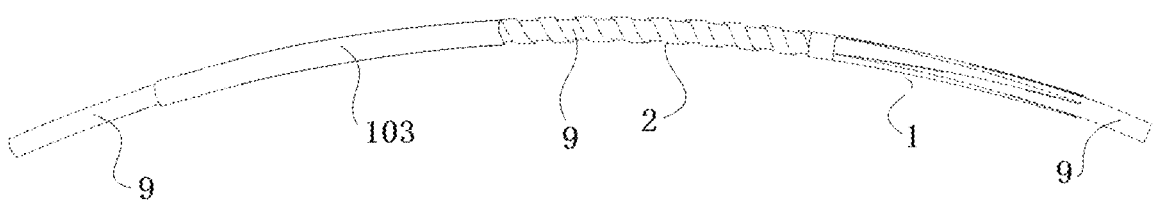
FIG. 6 is a schematic diagram illustrating the structure that an interventional guidewire is inserted in the structure according to Example 1 of the present disclosure at T0 temperature.
Figure 7:
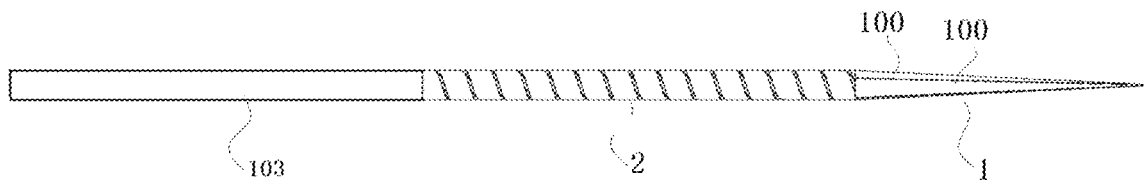
FIG. 7 is a schematic diagram illustrating the structure that an interventional guidewire is inserted in the structure according to Example 1 of the present disclosure at T1 temperature.

When in use, as shown in FIGS. 6-7, the metal spiral tube 2 of the puncture needle of the present disclosure, may be connected to the long tube 103 which may be a metal hollow tube, a plastic hollow tube, or a metal spiral tube, or hypotube. The length of the long tube needs to be 1 to 2 m, in order to allow it passing through the blood vessels to entry the tumor tissue in the body.

The free end of metal spiral tube 2 is fixedly connected (such as by laser welding) to the long tube 103 for specific use. When the temperature is T0 (such as 37° C.), the metal spiral tube 2 has a wider pitch, and there is a gap in the pitch between two adjacent spiral coils. Therefore, it has good flexibility, and the split-shaped structure is also in the opened state. The interventional guidewire 9 is passed through the free end of long tube, and out from the metal spiral tube 2 and the split-shaped structure 1, which corresponds to the tapered petals 100 are wrapped around the outer wall of the interventional guidewire, as shown in FIG. 6 (for clarity, the length of the long tube is drawn shorter). Due to the proper coordination of the width of the memory metal sheet in the metal spiral tube 2 and the gap between spiral coils, the guidewire can maintain the required strength and flexibility and pass through the blood vessels up to 1 to 2 m, to reach the tumor tissue in the body. Next, the interventional guidewire is withdrawn, and the physiological saline at temperature T1 (for example, 5° C.) is injected into the head portion of the puncture needle through the long tube, cooling the metal spiral tube and the split-shaped structure to temperature T1. Thereby, the pitch of the metal spiral tube is decreased, while the hardness is increased, and each of the tapered petals 100 in the split-shaped structure 1 is closed to form a needle-shaped structure or a conical structure, as shown in FIG. 7. The tightened metal spiral tube and the closed split-shaped are coordinated with each other, so that it has a higher strength, and thus can easily and accurately pierce the internal blood vessels of the tumor into the interior of tumor tissue. After entering the interior of the tumor, the physiological saline at the temperature T1 is stopped to be injected, so as to raise the temperature of the puncture needle gradually to T0. Thereby the pitch of the metal spiral tube is increased, and the multi-petals structure of the memory alloy is opened. Finally, the tissue fluid and tumor cells inside the tumor are taken out by passing through the puncture needle with a syringe or other instruments.

After stopping the injection of the physiological saline solution at the temperature T1, each of tapered petals opens with increasing temperature. Since each of tapered petals after the opening will have a tip end at the forefront, rotation or slight movement of the puncture needle will bring out a common puncture or agitation of the plurality of tapered petals, resulting in further pounding or smashing to the damaged tissue at its site. Therefore, the block structure of the tumor tissue is destroyed in the small area, so that it is convenient to take out this part of the tissue. Thus, when taking out the tissue fluid and tumor cells inside the tumor, effective tissue and effective amounts thereof can be obtained for detection, ensuring the success rate of the subsequent biopsy.

Example 2

Figure 8:
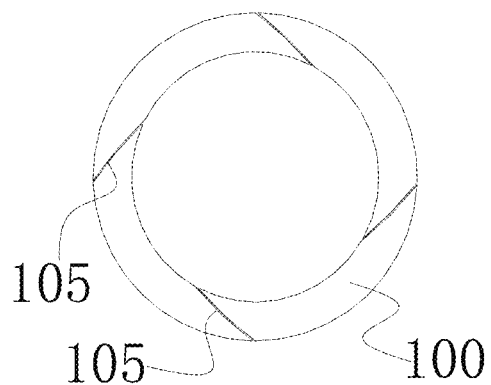
FIG. 8 is a cross-sectional diagram illustrating the split-shaped structure of Example 2 of the present disclosure in the closed state.
Figure 9:
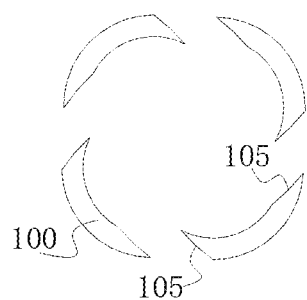
FIG. 9 is a cross-sectional diagram illustrating the split-shaped structure of Example 2 of the present disclosure in the opened state.
Figure 10:
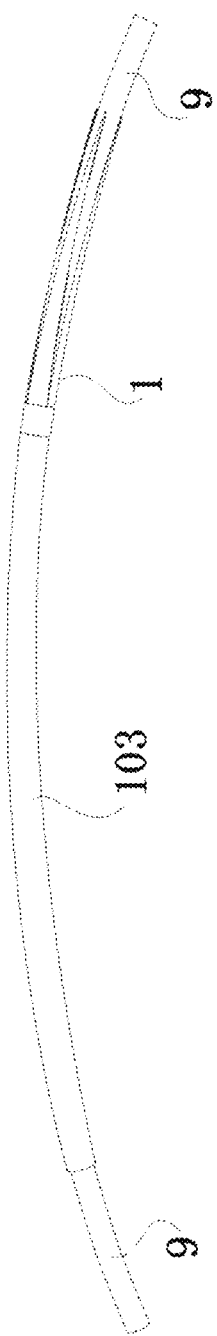
FIG. 10 is a schematic diagram illustrating the structure that a interventional guidewire is inserted in the structure according to Example 4 of the present disclosure when using.

On the basis of example 1, as shown in FIGS. 8-9, in the tapered petals 100, the sides for abutting or separating from the adjacent tapered petals are inclined faces 105. That is, one tapered petal 100 has two sides, each of which has a beveled configuration. And all the inclined faces 105 of the tapered petals 100 are consistent in direction (i.e., in the clockwise or counterclockwise direction), which ensures that the two abutted inclined faces in two adjacent tapered petals can be just fitted together. That is, one is gradually inclined outward from the inside, while the other is inclined inward from the outside, and thus the two can be just fitted together, so that the inner and the outer surfaces after being fitted together are smooth arced surfaces.

The design of the beveled configuration means that the width of the sides is widened, so that the contact area is increased when the two adjacent tapered petals are abutting each other, and the bonding strength is greater between tapered petals 100 after the split-shaped structure 1 is closed, obtaining a better puncture effect of the needle-shaped structure. More importantly, since the sides are designed as inclined faces 105, the contact width is increased when the two adjacent tapered petals 100 are abutting each other, and thus the physiological saline will not be sprinkled to the outside after closing, which can greatly reduce the amount of saline injected.

Example 3

On the basis of example 1 or 2, in the tapered petals 100, the side or inclined face 105 for abutting or separating from the adjacent tapered petals is provided with a first flexible layer, to make the abutment strength between the tapered petals more tight and the sealing therebetween better. The better sealing can extend the time of keeping the needle-shaped or conical structure, which makes the biopsy sampling more convenient.

As a further preferred embodiment, the inner side surface of the tip end of the tapered petal is provided with a second flexible layer, to make when the split-shaped structure is closed, the abutment strength between the tapered petals more tight and the sealing therebetween better, and when the interventional guidewire passed through the inner of the split-shaped structure, the bonding force with the interventional guidewire more stronger, and the integration effect is improved to increase the operation effect.

The first and second flexible layers may have a thickness of 0.005 to 0.04 mm, and the materials of the first and second flexible layers may be polytetrafluoroethylene or the like.

Example 4

The use of the intravascular memory metal puncture needle is provided. The system can be applied in the puncture of blood vessel wall in the human body, and in the biopsy sampling of blood vessel and tissue; the method for using it comprises:

(i) At temperature T0, increasing the pitch in the metal spiral tube, opening the split-shaped structure, and then inserting a interventional guidewire from a free end of the guide tube, passing through the metal spiral tube until out from the opened split-shaped structure, so that the structure is moving in the blood vessels of the body;

(ii) after reaching the site to be punctured, drawing out the interventional guidewire, inserting a syringe from the long tube, and injecting physiological saline at T1 temperature into the split-shaped structure when the injection needle reaches the puncture needle, and T1 is 5° C.; gradually closing the split-shaped structure when the temperature of the puncture needle is gradually decreased to 5° C. with the injection of physiological saline, so as to perform the puncture and sampling applications.

The system can be applied in the puncture of blood vessel walls in the human body. Specifically, it can puncture anywhere in any blood vessel of the human body, the purpose of which may be to detect, treat, observe or view the condition and so on. If there are congestions at some sites, the blood vessel walls at the corresponding site can be punctured, and thus the unabsorbable blood can be dispersed into the tissue to eliminate these congestions.

The system can be applied in the biopsy sampling of blood vessel and tissue: it can enter a tissue or an organ through blood vessels, and then pierce the blood vessel to enter the tissue or the organ, e.g., piercing the tumor blood vessels to enter the tumor tissue for biopsy or detecting sampling.

In this example, the piercing is a puncture of blood vessels, tissues or organs, and the puncture is basically a puncture of blood vessels or tissues or organs deep in the human body. The puncture of the body surface can be readily achieved by the method or technology in the prior art, while it is difficult and troublesome to reach the site deep in the human body. This disclosure can be applied to blood vessels, tissues and organs deep in the human body. Of course, when using, the puncture needle needs to be connected to the long tube and then the guide tube is inserted therein.

Example 5

In order to further study the practical effect of the puncture needle in this disclosure, the applicant has carried out from various aspects, such as the type and length of the blood vessels to be passed through, the passing time, the damage to the blood vessel, the strength of the tip, the sampling time and the accuracy, and so on.

Method:

taking the biopsy for liver tumor sampling as an example, through the Seldinger arterial puncture technique, under the guidance of radiography, the interventional guidewire passes through the puncture needle at the T0 temperature (such as 37° C.). Usually, guidewire passes from the cavity of the long tube and out from the middle of the split-shaped structure, and then enters the hepatic artery via the femoral artery under the coordination of the guidewire, the long tube and the split-shaped structure, then enters the liver blood vessel from the liver artery, and finally enters the inside of the tumor blood vessels. The interventional guidewire is withdrawn, and at the temperature of T1 (such as 5° C.), the puncture needle is pierced through the internal blood vessels of the tumor and enters the tumor tissue. Next, the physiological saline of T1 temperature is stopped injecting, the temperature is raised to the T0 temperature, the puncture needle is opened, and then the sampling is carried out. A biopsy test is performed with the taken tumor tissue or tissue fluid.

In the above process, the types of blood vessels passed through are: femoral artery-hepatic artery-liver blood vessel-internal blood vessel in the tumor.

The length of the blood vessel passed through: 1.6 m.

The puncture needles of examples 1 to 3 are tested as the experimental groups 1 to 3 respectively. Finally, the passing time, the damage to the blood vessel, the strength of the tip, the sampling time, and the accuracy are measured.

Comparative Example 1: the split-shaped structure in example 1 is only employed, and there is no metal spiral tube. In use, the tail end of the split-shaped structure is connected to the long tube, as shown in FIG. 9.

Comparative Example 2: the width b of the memory alloy sheet for making the spiral coil of example 1 is changed to 2 mm. When the spiral coil is loosened (i.e., at T0 temperature), the gap c between two adjacent spiral coils is 1 mm.

Comparative Example 3: the width b of the memory alloy sheet for making the spiral coil of example 1 is changed to 0.1 mm. When the spiral coil is loosened (i.e., at T0 temperature), the gap c between two adjacent spiral coils is 1 mm.

Comparative Example 4: the structure of example 1 is changed to a conical structure as the split-shaped structure is closed, and the memory alloy is not used. Therefore, this example always is conical structure whether it passes through the blood vessel or punctures the tumor tissue. During passaging through the blood vessel, the interventional guidewire cannot pass out from the conical structure, so it abuts against the inside of the conical structure. In addition, the metal spiral tube is the same with that in example 1.

Comparative Example 5: the structure of example 1 is changed to the structure as the split-shaped structure is opened, and the memory alloy is not used. Therefore, this example always is opened structure whether it passes through the blood vessel or punctures the tumor tissue. During passaging through the blood vessel, the interventional guidewire passes out the conical structure. When entering the tumor tissue, various tapered petals also are opened. In addition, the metal spiral tube is the same with that in example 1.

Comparative Example 6: the memory metal spiral tube of example 1 is changed to a spring which has same flexibility with the memory metal spiral tube, but is not made of memory alloy. This spring has the same intensity as that of the metal spiral tube in Example 3 at the T0 temperature.

Comparative Example 7: the memory metal spiral tube of example 1 is changed to a spring which is not made of memory alloy. This spring has the same intensity as that of the metal spiral tube in Example 3 at the T1 temperature.

The results of the above examples are summarized in the table below.

In the above table, i) the time to reach the tumor blood vessels refers to the time required to reach the tumor tissue by passing through the blood vessel in each example and the comparative example, in the case where the long tube is completely identical; ii) the damage to the blood vessel refers to the case of scratching or stabbing inside the blood vessel; iii) the tip strength when puncturing refers to the force of the head portion of the puncture needle when puncturing the inner wall of the tumor blood vessels; iv) the accuracy of the puncturing refers to the closeness between the actual puncturing site in the blood vessel and pre-puncturing site in the blood vessel. The value is close to 100%, the accuracy is higher. When repeatedly puncturing, the better the superimposition effect is, the easier the puncturing is; v) the sampling time refers to the time taken by the sampling device such as a syringe to take a sample; vi) the precision of biopsy refers to that the precision reaches 100% when the effective amount of the tumor tissue is obtained. The reason affecting the precision of biopsy is basically in structural limitation, which lead to the local destruction to tumor tissue is weak, the effective amount of tumor tissue taken out is too small, and thus the precision of detection is low; vii) the amount of saline injected at the T1 temperature refers to the amount required to close the head portion of the puncture needle and maintain the closed state.

The results of the above experimental and comparative groups are explained as follows:

Example 1: the structure can smoothly pass through a long femoral artery, a hepatic artery and enter the tumor blood vessels. This structure flexibility moves in the blood vessel, and can puncture the blood vessel wall earlier. Many times, the blood vessel wall can be pierced once and the precision is high. If it is not pierced at the first time, it will be pierced easily at the second time. Since all of four tips are capable of directionally and locally destroying the tumor tissue, the sampling time is short and an effective amount of tumor tissues can be obtained. The precision of biopsy can be about 100% (precluding factors such as human error or mistake in the detection).

Example 2: the structure can smoothly pass through the tried femoral artery, hepatic artery and enter the tumor blood vessels. This structure can move in the blood vessel more flexible, and can puncture the blood vessel wall earlier. Both the precision and the biopsy accuracy are high. Due to the good sealing performance of the puncture needle, the amount of physiological saline that needs to be injected to maintain the T1 temperature is small.

Example 3: the structure can smoothly pass through the tried femoral artery, hepatic artery and enter the tumor blood

|  | Time to reach tumor blood vessels/min | Damage to blood vessels | Strength of tip when puncturing/ N | Accuracy of puncture | Time for puncturing blood vessel wall and entering tumor | Sampling time/ | Precision of biopsy/ % | Amount of saline injected at T1 temperature/ ml |
|---|---|---|---|---|---|---|---|---|
| Ex. 1 | 5-10 | 5% | 2.8N | 99-100% | 3-8 s | 10-40 s | 100% | 15-20 ml |
| Ex. 2 | 5-10 | 5% | 2.9N | 100% | 3-8 s | 10-40 s | 100% | 5-15 ml |
| Ex. 3 | 5-10 | 4% | 2.9N | 100% | 3-8 s | 10-40 s | 100% | 5-10 ml |
| Ex. 1 | 10-15 | 6% | 2N | 94% | 10-15 s | 10-40 s | 100% | 15-20 ml |
| Com. ex 2 | 20-30 | 8% | 2.8N | 99-100% | 3-8 s | 10-40 s | 100% | 5-15 ml |
| Com. ex 3 | 15-25 | 5% | 1.5N | 90% | 10-25 s | 15-40 s | 99-100% | 15-25 ml |
| Com. ex 4 | 20-35 | 35% | 2N | 95% | 10-20 s | 1-4 min | >95% | none |
| Com. ex 5 | 10-15 | 6% | 0.8N | 85-90% | >50 s | — | — | none |
| Com. ex 6 | 5-10 | 5% | 1.1N | 50-70% | 40-60 s | 20-70 s | >90% | 15-20 ml |
| Com. ex 7 | 15-25 | 15% | 1.5-2.5N | 80-95% | 10-40 s | 15-60 s | 100% | 15-20 ml | vessels. This structure can move in the blood vessel more flexible, and can puncture the blood vessel wall earlier. Both the precision and the biopsy accuracy are high. Due to the good sealing performance of the puncture needle, the amount of physiological saline that needs to be injected to maintain the T1 temperature is small.

Comparative Example 1: the structure basically can pass through a long femoral artery, a hepatic artery and enter the tumor blood vessels smoothly. The degree of the damage to the blood vessels is small. The strength of the tip can ensure the puncture of the blood vessel wall, and the precision is high. Since all of four tips are capable of directionally and locally destroying the tumor tissue, the sampling time is short and an effective amount of tumor tissues can be obtained. The precision of biopsy can be about 100% (precluding factors such as human error or mistake in the detection).

Comparative Example 2: since the width b of the memory alloy sheet is increased, the flexibility will be decreased. Although the gap c between the pitches is increased, as the width b is too wider, the flexibility is greatly decreased locally. Therefore, when moving in the blood vessel with a large curvature, the degree of damage to the blood vessel wall is greatly increased. Thus, the smoothness of moving in the blood vessel is reduced, and the moving time is increased.

Comparative Example 3: i) since the width b of the memory alloy sheet is decreased and the gap c is increased, the strength is relative low, and the moving time will be increased. ii) since the width b is too narrow, the strength is too low even if the spiral coils are abutted together. In addition, the strength of the tip end is also too low. In addition, the precision of puncturing is greatly reduced, and thus time for entering the tumor via puncturing the blood vessel wall is greatly increased. When the strength is lowered, the time for damaging the local tumor tissue for sampling will also be increased overall.

Comparative Example 4: i) the tip structure that moves in a straight line will cause serious damage to blood vessels, and will greatly affect the moving time; the interventional guidewire neither can be guided out, nor can function as a front guide, and thus will greatly increase the movement time in the blood vessels. ii) Because there is only one tip at the tip end, the local destruction effect on the tumor tissue is poor, so it is difficult to obtain an effective tumor tissue sample during sampling, resulting in an increase in sampling time. iii) Due to the long sampling time, the amount of tumor tissue in the sample taken sometimes is too small, resulting in a decrease in accuracy. iv) In addition, since the tip causes serious damage to the blood vessel, it is necessary to pay special attention when moving in the blood vessel, and thus the moving time is greatly increased.

Comparative Example 5: i) Since the four tips at four tapered petals are scattered at four places, instead of the same places, the tip strength is small and thus it is not easy to pierce the blood vessel wall. Even if it is pierced, it is not easy to pass through the blood vessel to enter the tumor tissue. ii) Because the tip strength is small, it is difficult to control the force thereof. Therefore, it usually requires multiple piercings to enter the tumor tissue. The accuracy of piercing the blood vessel is significantly lowed. iii) It takes a long time to pierce the blood vessel wall and enter the tumor tissue. In many cases, even if it pierces the blood vessel wall, it cannot enter the tumor tissue. iv) Because the entire needle cannot enter the tumor tissue through the blood vessel, it is difficult to obtain an effective tumor tissue and thus cannot used in the clinic.

Comparative Example 6: i) The tip itself has certain strength, but the back thereof is supported by a spring. The spring when applying force is operated remotely due to its elastic force. Therefore, the strength is not enough, and the point to be applied force is not easy to be controlled. Under the action of elastic force, when the force is applied, the spring is easy to bend, and the force is easily dispersed from different directions, so that the piercing force is greatly reduced. As the force at the tip is small, it is difficult to pierce the blood vessel inner wall. Therefore, it needs many times to pierce the blood vessel inner wall, or even cannot pierce the blood vessel inner wall. ii) The precision of piercing the blood vessel wall is poor, and the sites at the different piercings are different, so it is difficult to achieve the piercing each time. iii) Because of the poor precision of piercing the blood vessel wall at different times, the previous several piercings have little auxiliary effect on the subsequent piercings. And since the force required for each piercing is consistent, the piercing time is greatly increased; the damage to the blood vessel wall is also serious when piercing. iv) Due to the elastic force of the spring, it is difficult to control the direction of the force, so the directional damage to the local tumor tissue is poor; and it takes a long time to obtain effective tumor tissue. In addition, the stability is also poor. v) Due to the long sampling time, sometimes the amount of tumor tissue in the sample taken is too small, resulting in a decrease in accuracy.

Comparative Example 7: As the tenacity is lowered, the moving flexibility in the blood vessels is lowered, and the degree of damage to the inside of the blood vessels is increased. Even if the strength of the spring is the same with that in example 1 at the T1 temperature, the force on the spring is difficult to maintain consistency in all directions when piercing. The force is usually dispersed in different directions due to the intrinsic property of the spring, significantly lowering the strength of the tip, reducing the precision of piercing, and increasing the piercing time. In short, the strength, precision and piercing time are unstable, sometimes it is ideal, sometimes it is very laborious. Poor stability is shown in the practices. In addition, it also has a certain impact on the sampling time. Moreover, since the tip has serious damage to the blood vessel, it is necessary to pay special attention when moving in the blood vessel, and thus the moving time is greatly increased.

The data in the Example are the average values obtained by multiple experiments. For the degree of damage within 10%, the human health will not be affected, and the damage can be healed itself in about 24 h. Moreover, the puncture needle in the example of the present disclosure has quite accuracy in the process of piercing the blood vessel, and only needs to pierce a small hole to pass through the blood vessel wall. Due to the elasticity and self-repairing of the blood vessel, the damage in the example of the present disclosure can be self-healing. However, regarding comparative example, it can cause damage during the transmission, and cause a serious local damage the blood vessel wall after the piercing as the precision is not enough or the force control in a certain direction is inconvenient. Many times it needs to add drugs, such as embolic agents for interventional therapy.

In the present disclosure, the out diameter of interventional guidewire 9 is not larger than the inner diameter of long tube and the head portion of the needle. The interventional guidewire 9 is made of stainless steel core. The interventional guidewire 9 may comprise a winding layer wrapped around the periphery of the stainless steel core, and the winding layer is composed of at least one winding wire wrapped around the periphery of the stainless steel core. A hydrophilic layer may also be applied around the winding layer, to make the front end portion of the split-shaped structure moving in the blood vessel smoother. A polymer layer may be provided between the hydrophilic layer and the winding layer. The material of the hydrophilic layer may be polytetrafluoroethylene, silicone rubber, polyethylene, polyvinyl chloride, fluorocarbon polymer, or polyurethane and so on.

In the present disclosure, at T0 (such as 37° C.), the split-shaped structure is prefabricated into an opened state, and the metal spiral tube is prefabricated into a spirally loosened state; then at T1 (such as 5° C.), the split-shaped structure is prefabricated into a closed state, and the metal spiral pipe is prefabricated into a screwed state. The specific prefabrication method can be referred to the prior art.

The above description is only a preferred embodiment of the present disclosure, and is not intended to limit the present disclosure. It should be appreciated that various modifications and changes can be made to the present disclosure. Any modifications, equivalents, improvements, etc. made within the spirit and scope of the present disclosure are intended to be included within the scope of the present disclosure.

The invention claimed is:

1. An intravascular memory metal puncture needle, wherein the puncture needle comprises a split-shaped structure capable of opening and closing, as well as a metal spiral hollow tube including a plurality of spiral coils, wherein the split-shaped structure and the metal spiral hollow tube are made of memory metal, and the split-shaped structure is composed of a plurality of tapered petals;
   when a temperature is T1, a pitch between two adjacent spiral coils of the metal spiral hollow tube is decreased, each of the tapered petals of the split-shaped structure is closed, and thus the split-shaped structure exhibits a conical structure, to increase a strength of the split-shaped structure to pierce walls of blood vessels;
   when the temperature is T0, the pitch between two adjacent spiral coils of the metal spiral hollow tube is increased to enhance flexibility of the metal spiral hollow tube, thereby enabling the metal spiral hollow tube to move in the blood vessels of a body, and each of the tapered petals is opened to allow an interventional guidewire to pass through during using of the intravascular memory metal puncture needle, the split-shaped structure after opening is a cylindrical structure having a plurality of tapered notches on a wall of the cylindrical structure, and a center of the cylindrical structure is an open cavity structure.

2. The intravascular memory metal puncture needle according to claim 1, wherein an end with a larger diameter of the split-shaped structure is integrally connected to the metal spiral hollow tube; and the tapered petals have identical curvature and are formed by arc-shaped surfaces.

3. The intravascular memory metal puncture needle according to claim 2, wherein all of the tapered petals are identical in of shape and size.

4. The intravascular memory metal puncture needle according to claim 1, wherein when the temperature is T1, two adjacent spiral coils of the metal spiral hollow tube are closely abutted to form a more sealed structure, each of the tapered petals is closed, and two adjacent sides of two adjacent tapered petals are closely abutted, and then the split-shaped structure constitutes a fully enclosed conical structure; when the temperature is T0 and each of the tapered petals is opened, diameters of the tapered petals are substantially consistent throughout, and are substantially consistent with diameter of the metal spiral hollow tube.

5. The intravascular memory metal puncture needle according to claim 1, wherein the tapered petal comprises a tail end and a tip end, has a width gradually decreased from the tail end to the tip end; when each of the tapered petals is closed, a diameter of the tail end is larger than a diameter of the tip end;
   wherein the temperature of T0 is 37° C., and the temperature of T1 is 5° C.

6. The intravascular memory metal puncture needle according to claim 1, wherein the spiral coils of the metal spiral hollow tube are made by a memory alloy sheet having a width b of 0.3 to 1 mm; when the spiral coils of the metal spiral hollow tube are loosened, a gap c between two adjacent spiral coils is 0.05 to 0.2 mm;
   when the pitch of the metal spiral hollow tube is decreased, the gap c between two adjacent spiral coils is less than 0.001 mm or no gap is between two adjacent spiral coil.

7. The intravascular memory metal puncture needle according to claim 1, wherein the metal spiral hollow tube has a length of 4 to 10 mm; the split-shaped structure has a length of 3 to 10 mm; and when each of the tapered petals of the split-shaped structure is opened, the split-shaped structure has an outer diameter of 0.4 mm and an inner diameter of 0.3 mm.

8. The intravascular memory metal puncture needle according to claim 7, wherein sides of the tapered petals for abutting or separating from adjacent tapered petals are inclined faces, and all the inclined faces of the tapered petals are consistent in direction.

9. Use of the intravascular memory metal puncture needle according to claim 1, wherein the puncture needle is used for puncturing blood vessels or tissues or organs in a human body, and is used in a biopsy sampling of tumor in vivo, wherein a method for using the puncture needle comprises:
   (i) welding the metal spiral hollow tube of the puncture needle with a long tube;
   (ii) when the temperature of T0 is 37° C., increasing the pitch of the metal spiral hollow tube to open, the split-shaped structure, and then inserting a interventional guidewire from a free end of the long tube, through the metal spiral tube, and finally until out of the opened split-shaped structure, so that the split-shaped structure is moving in the blood vessels of the body;
   (iii) after reaching a site to be punctured, drawing out the interventional guidewire, inserting a syringe from the long tube, and respectively injecting a physiological saline at the temperature of T1 into the metal spiral hollow tube and the split-shaped structure when a needle of the syringe reaches the puncture needle, and T1 is 5° C.;
   gradually closing the split-shaped structure when a temperature of the puncture needle is gradually decreased to 5° C. with the physiological saline being injected, gradually decreasing the pitch of the metal spiral hollow tube, and closing the split-shaped structure, so as to perform puncture and sampling applications.

* * * * *